United States Patent [19]

Charpentier et al.

[11] Patent Number: 5,702,710
[45] Date of Patent: Dec. 30, 1997

[54] DIBENZOFURAN COMPOUNDS AND PHARMACEUTICAL/COSMETIC COMPOSITIONS COMPRISED THEREOF

[75] Inventors: Bruno Charpentier, Biot; Michèle Vion, Grasse Le Plan; Bruno Bernard, Neuilly Sur Seine; Jean Maignan, Tremblay En France, all of France

[73] Assignee: Centre International de Recherches Dermatologiques Galderma, Valbonne, France

[21] Appl. No.: 539,222

[22] Filed: Oct. 4, 1995

[30] Foreign Application Priority Data

Oct. 4, 1994 [FR] France ................... 94 11853
Oct. 28, 1994 [FR] France ................... 94 12989

[51] Int. Cl.⁶ ............................. A61K 7/48; C07D 307/79
[52] U.S. Cl. ........................ 424/401; 424/43; 424/59; 424/701; 424/443; 424/450; 424/456; 424/484; 424/489; 514/844; 514/846; 514/859; 514/886; 514/912; 514/937; 514/944; 549/457
[58] Field of Search ........................ 424/401, 443, 424/43, 59, 701, 450, 456, 484, 489; 549/457; 514/844, 846, 859, 886, 912, 937, 944

[56] References Cited

FOREIGN PATENT DOCUMENTS 0360637  3/1990  European Pat. Off. .
2187455  9/1987  United Kingdom .

*Primary Examiner*—Jyothsan Venkat
*Attorney, Agent, or Firm*—Burns, Doane, Swecker & Mathis, L.L.P.

[57] ABSTRACT

Novel pharmaceutically/cosmetically-active dibenzofuran compounds have the structural formula (I):

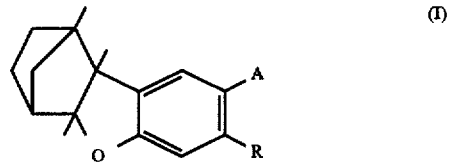

wherein A is a radical having one of the formulae (IIa), (IIb) or (IIc):

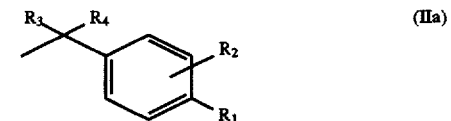

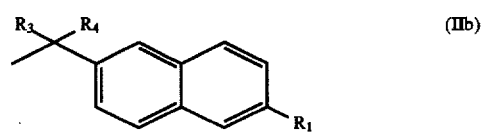

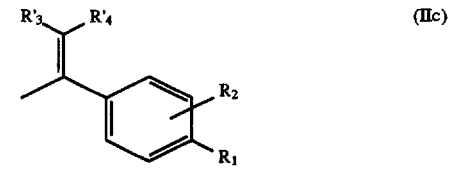

and are useful for the treatment of a wide variety of disease states, whether human or veterinary, for example dermatological, rheumatic, respiratory, cardiovascular and ophthalmological disorders, as well as for the treatment of mammalian skin and hair conditions/disorders.

28 Claims, No Drawings

DIBENZOFURAN COMPOUNDS AND PHARMACEUTICAL/COSMETIC COMPOSITIONS COMPRISED THEREOF

BACKGROUND OF THE INVENTION

TECHNICAL FIELD OF THE INVENTION

The present invention relates to novel polycyclic dibenzofuran compounds and to pharmaceutical/cosmetic compositions comprised thereof; the subject compounds are especially useful in human or veterinary medicine, or, alternatively, in cosmetic compositions.

SUMMARY OF THE INVENTION

The compounds according to the invention display marked activity in the fields of cell differentiation and proliferation, and are particularly useful in the topical and systemic treatment of dermatological conditions associated with a keratinization disorder, dermatological conditions (and the like) including an inflammatory, viral and/or immunoallergic component, and dermal or epidermal proliferations, whether benign or malignant. The subject compounds can, in addition be used for the treatment of degenerative diseases of the connective tissue, for controlling or combating aging of the skin, whether photoinduced or chronologic, and for treating cicatrization disorders. They are also useful for ophthalmological applications, especially for the treatment of corneopathies.

The compounds according to this invention can also be formulated into cosmetic compositions, especially for body and hair care.

Briefly, the dibenzofuran compounds according to this invention have the following structural formula (I):

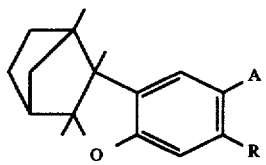

(I)

in which R is a hydrogen atom, a halogen atom, a lower alkyl radical, a lower acyl radical or an OR' radical, with R' having the definition given below; A is a radical selected from among those of the following formulae (IIa–IIc):

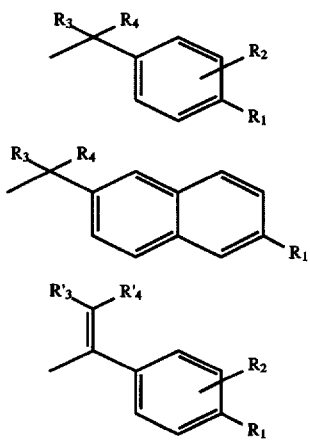

wherein $R_1$ is (i) a hydrogen atom, (ii) the —$CH_3$ radical, (iii) a —$CH_2$—O—$R_5$ radical, (iv) an —$OR_5$ radical (v) a

radical, (vi) an —$S(O)_t R_6$ radical, with t, $R_5$ and $R_6$ having the definitions given below; $R_2$ is a hydrogen atom or the —$OR_5$ radical, with $R_5$ having the definition given below; $R_3$ and $R_4$ are independently a hydrogen atom, a lower alkyl radical or the —$(X)_n$—$(CH_2)_m$—$R_7$ radical, with X and $R_7$ having the definitions given below, with the proviso that $R_3$ and $R_4$ may together form an oxo (=O) group, a thioxo (=S) group, an oxime group or a group derived from the oxime ($R_6$—O—N=), an epoxy group, a cycloalkyl group optionally substituted by a halogen atom or a lower alkyl radical, or a dioxolane group [—O—$(CH_2)_q$—O—] wherein q is equal to 2 or 3, with $R_6$ having the definition given below; $R_3'$ and $R_4'$ are independently a hydrogen atom, a lower alkyl radical or a lower acyl radical; t is equal to 0, 1 or 2; $R_5$ is a hydrogen atom, a lower alkyl radical, or a lower acyl radical; $R_6$ is a hydrogen atom, an —$N(R',R''')$ radical, with R' and R''' having the definitions given below, or an —$OR_8$ radical, with $R_8$ having the definition given below; $R_7$ is a hydrogen atom or a —$(CO)_p$—$R_9$ radical, wherein p is 0 or 1, with $R_9$ having the definition given below; $R_8$ and R' are independently a hydrogen atom, an alkyl radical having from 1 to 20 carbon atoms, a mono- or polyhydroxyalkyl radical, an optionally substituted aryl or optionally substituted aralkyl radical, a sugar residue, or an amino acid residue; $R_9$ is a hydrogen atom, an alkyl radical, an alkenyl radical, an alkynyl radical, an aryl radical, an —$OR_7$ radical wherein m is other than 0, with $R_7$ having the definition indicated above, or an —$N(R',R''')$ radical, with R' and R''' having the definitions given below; R' and R''', which may be identical or different, are each a hydrogen atom, a lower alkyl radical, a mono- or polyhydroxyalkyl radical, an optionally substituted aryl radical, an optionally substituted aralkyl radical or an amino acid or peptide or sugar residue, with the proviso that R' and R''' may together form a heterocycle; X is an oxygen or sulfur atom; and n ranges from 0 to 1 and m from 0 to 10.

This invention also features the optical and geometrical isomers of the compounds of formula (I), as well as their salts in the event that $R_1$ or $R_9$ represents an acid functional group, or when $R_9$ represents an amine functional group.

When the compounds according to the invention are in the form of salts, by addition of a base, they are preferably salts of an alkali metal or alkaline earth metal, or, alternatively, of zinc or of an organic amine.

When the compounds of the invention are in the form of salts, by addition of an acid, they are pharmaceutically or cosmetically acceptable salts of an inorganic or organic acid, in particular of hydrochloric, sulfuric, acetic, citric, fumaric, hemisuccinic, maleic and mandelic acid.

DETAILED DESCRIPTION OF BEST MODE AND PREFERRED EMBODIMENTS OF THE INVENTION

More particularly according to the present invention, by "lower alkyl radical" is intended an alkyl radical having from 1 to 6 carbon atoms and preferably the methyl, ethyl, isopropyl, butyl, tert-butyl and hexyl radicals.

By "alkenyl radical" is intended a linear or branched radical having from 1 to 20 carbon atoms and containing at least one ethylenic double bond.

By "alkynyl radical" is intended a linear or branched radical having from 1 to 20 carbon atoms and containing at least one acetylenic triple bond.

By "lower acyl radical" is intended a radical having from 1 to 10 carbon atoms and preferably the acetyl, propionyl and pivaloyl radicals.

By "alkyl radical" is intended a linear or branched radical having from 1 to 20 carbon atoms, optionally substituted by one or more fluorine atoms.

By "monohydroxyalkyl radical" is intended a radical having from 1 to 6 carbon atoms, especially a 2-hydroxyethyl, 2-hydroxypropyl or 3-hydroxypropyl radical.

By "polyhydroxyalkyl radical" is intended a radical having from 2 to 6 carbon atoms and from 2 to 5 hydroxyl groups, such as the 2,3-dihydroxypropyl, 2,3,4-trihydroxybutyl or 2,3,4,5-tetrahydroxypentyl radicals, or a pentaerythritol residue.

By "aryl radical" is preferably intended a phenyl radical optionally substituted by one or more halogen atoms, a hydroxyl or nitro functional group or a methoxy group.

By "aralkyl radical" is intended a benzyl or phenethyl radical, optionally substituted by one or more halogen atoms, a hydroxyl or nitro functional group, or a methoxy group.

By "amino acid residue" is intended a residue derived, for example, from one of the 20 amino acids of L or D configuration from which mammalian proteins are constructed.

By "peptide residue" is intended a linear peptide comprising from 2 to 10 amino acids.

By "sugar residue" is intended a residue derived, for example, from glucose, galactose, mannose, or glucuronic acid.

Lastly, by "heterocycle" is preferably intended a piperidino, morpholino, pyrrolidino or piperazino radical, optionally substituted at the 4-position by a $C_1$–$C_6$ alkyl radical, or a mono- or polyhydroxyalkyl radical as defined above.

Among the compounds of formula (I), particularly representative are the following:

Methyl 6-[(1,2,3,4-tetrahydro-1,4a,9b-trimethyl-1,4-methanodibenzofuran-8-yl)carbonyl]-2-naphthoate;

6-[(1,2,3,4-Tetrahydro-1,4a,9b-trimethyl-1,4-methanodibenzofuran-8-yl)carbonyl]-2-naphthoic acid;

6-[(1,2,3,4-Tetrahydro-1,4a,9b-trimethyl-1,4-methanodibenzofuran-8-yl)methyl]-2-naphthoic acid;

Methyl 6-[(1,2,3,4-tetrahydro-1,4a,9b-trimethyl-1,4-methanodibenzofuran-8-yl)hydroxymethyl]-2-naphthoate;

6-[(1,2,3,4-Tetrahydro-1,4a,9b-trimethyl-1,4-methanodibenzofuran-8-yl)hydroxymethyl]-2-naphthoic acid;

Methyl 4-[(1,2,3,4-tetrahydro-1,4a,9b-trimethyl-1,4-methanodibenzofuran-8-yl)carbonyl]benzoate;

4-[(1,2,3,4-Tetrahydro-1,4a,9b-trimethyl-1,4-methanodibenzofuran-8-yl)carbonyl]benzoic acid;

4-[(1,2,3,4-Tetrahydro-1,4a,9b-trimethyl-1,4-methanodibenzofuran-8-yl)hydroxymethyl]phenylcarbinol;

4-[(1,2,3,4-Tetrahydro-1,4a,9b-trimethyl-1,4-methanodibenzofuran-8-yl)carbonyl]benzaldehyde;

2-(1,2,3,4-Tetrahydro-1,4a,9b-trimethyl-1,4-methanodibenzofuran-8-yl)-2-(4-methoxycarbonylphenyl)-1,3-dioxolane;

2-(1,2,3,4-Tetrahydro-1,4a,9b-trimethyl-1,4-methanodibenzofuran-8-yl)-2-(4-carboxyphenyl)-1,3-dioxolane;

1,2,3,4-Tetrahydro-1,4a,7,9b-tetramethyl-1,4-methanodibenzofuran;

Methyl 4-[(1,2,3,4-tetrahydro-1,4a,7,9b-tetramethyl-1,4-methanodibenzofuran-8-yl)carbonyl]benzoate;

4-[(1,2,3,4-Tetrahydro-1,4a,7,9b-tetramethyl-1,4-methanodibenzofuran-8-yl)carbonyl]benzoic acid.

According to the present invention, the preferred compounds of formula (I) are those in which A is the radical of formula (IIb).

The more particularly preferred compounds are those in which A is the radical of formula (IIb) in which $R_1$ is the

radical.

The present invention also features novel intermediate compounds, namely, those compounds having the following structural formula (X):

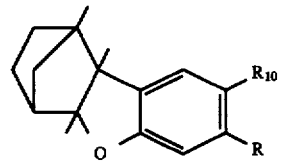

(X)

in which R has the definition of R in the compounds of formula (I), $R_{10}$ has the definition of $R_1$ described above, other than a hydrogen atom, or $R_{10}$ can also be a halogen atom, the —C(O)—$R_8$ radical, or the —C(O)—$CH_2$—halogen or $(CH_2)_nN(R',R''')$ radical, wherein $R_8$, R" and R"' are as defined in formula (I).

Particularly exemplary compounds (X) include:

1,2,3,4-Tetrahydro-1,4a,9b-trimethyl-1,4-methanodibenzofuran-8-yl methyl ketone;

1,2,3,4-Tetrahydro-1,4a,9b-trimethyl-1,4-methanodibenzofuran-8-carboxaldehyde;

1,2,3,4-Tetrahydro-1,4a,9b-trimethyl-1,4-methanodibenzofuran-8-carboxylic acid;

1,2,3,4-Tetrahydro-1,4a,9b-trimethyl-1,4-methanodibenzofuran-8-yl bromomethyl ketone;

8-Ethynyl-1,2,3,4-tetrahydro-1,4a,9b-trimethyl-1,4-methanodibenzofuran.

The present invention also features the processes for the preparation of the compounds of formula (I), comprising a Friedel-Crafts reaction between 1,2,3,4-tetrahydro-1,4a,9b-trimethyl-1,4-methanodibenzofuran, or a substituted derivative of this nucleus of formula (III) (family of the compounds of formula (X)) and an acid chloride of structural formula (IV) or (V) (see reaction scheme below).

1,2,3,4-Tetrahydro-1,4a,9b-trimethyl-1,4-methanodibenzofuran (THTMDBF) is prepared in two stages, i.e., by addition of o-anisyllithium to fenchone, followed by reaction with phosphorus pentachloride, phosphorus tribromide or a Lewis acid. The fenchone can be dextrorotatory or levorotatory.

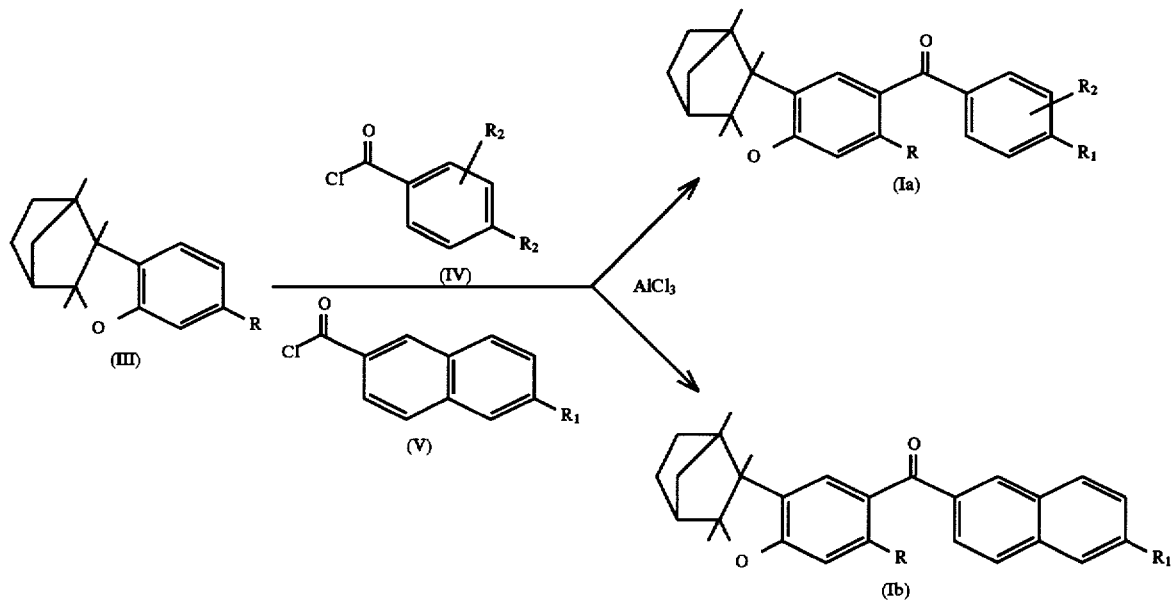

The compounds of formulae (Ia) and (Ib) correspond to those of formula (I) in which A respectively represents the radicals of formulae (IIa) and (IIb), in which $R_3$ and $R_4$ together form an oxo group.

The compounds of formula (I) can also be prepared by reacting an organometallic derivative in the 8-position of the nucleus (formula III), such as an organozinc or an organotin compound (formula VII), with a compound of formula (IV) or (V), catalyzed by a palladium derivative, according to the following reaction scheme:

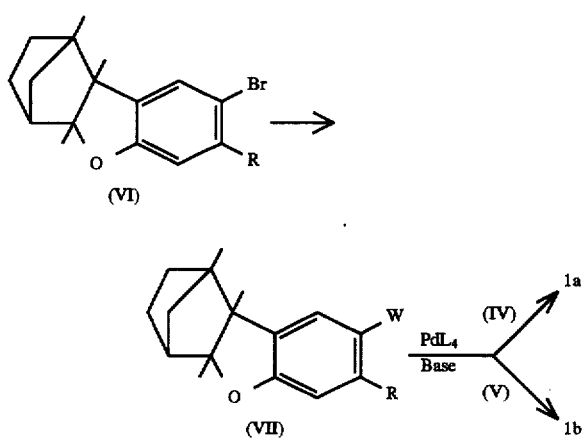

W = —ZnCl; —Sn(nBu)₃

The compounds of formula (I) can also be prepared via carbonylation, according to the following reaction scheme:

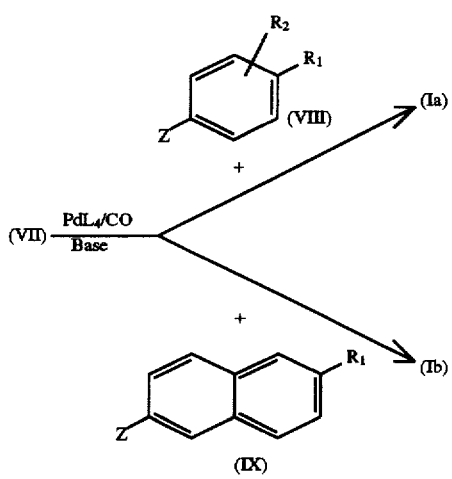

In the formulae (VIII) and (IX), Z is Br, I or O—SO₂—CF₃.

During these reactions for the preparation of the compounds of formula (I), the $R_1$ and $R_2$ functional groups will optionally be protected in order to be compatible with the operating conditions. The protecting groups employed are those described in the text *Protecting Groups in Organic Synthesis*, by T. W. Greene, published by John Wiley and Sons (1981).

The derivatives (Ia) and (Ib) are subsequently used as starting materials for the preparation of other compounds according to conventional techniques of organic chemistry, such as those described in the text *Advanced Organic Chemistry*, by J. March, John Wiley and Sons (1985). In particular, a modification of the carbonyl functional group will provide the various definitions of $R_3$ and $R_4$.

These compounds exhibit partial agonist or antagonist activity with respect to the expression of one or more biological markers in the test of differentiation of embryonic teratocarcinoma cells (F9) in mice (*Skin Pharmacol.*, 3, p. 256–267 (1990)) and/or on the in vitro differentiation of human keratinocytes (*Skin Pharmacol.*, 3, p. 70–85 (1990)), in response to treatment with retinoids. These tests demonstrate the activities of the subject compounds in the fields of differentiation and of proliferation. The noted activities can also be measured in cell transactivation tests using previously transfected recombinant RAR or RXR receptors (B. A. Bernard et al, *Biochemical and Biophysical Research Communication*, vol. 186, 977–983 (1992); M. F. Boehm et al, *Journal of Medicinal Chemistry*, 37, 408–414 (1994)).

The present invention also features therapeutic/pharmaceutical applications of the compounds of formula (I).

The compounds according to the invention are particularly well suited in the following fields of therapy:

(1) for treating dermatological conditions associated with a keratinization disorder involving differentiation and proliferation, in particular for treating acne vulgaris, comedonic or polymorphic acne, acne rosacea, nodulocystic acne, acne conglobata, senile acne and secondary acnes such as solar, drug or occupational acne;

(2) for treating other types of keratinization disorders, in particular ichthyoses, ichthyosiform conditions, Darier's disease, palmoplantar keratoderma, leucoplakia and leucoplakiform conditions, or cutaneous or mucosal (oral) lichen;

(3) for treating other dermatological conditions associated with a keratinization disorder and manifesting an inflammatory and/or immunoallergic component and, in particular, all forms of psoriasis, either cutaneous, mucosal or ungual, and even psoriatic rheumatism, or, alternatively, cutaneous atopy, such as eczema, or respiratory atopy or gingival hypertrophy; the compounds can also be used for treating certain inflammatory conditions which do not exhibit keratinization disorder;

(4) for treating all dermal or epidermal proliferations, whether benign or malignant, whether or not of viral origin, such as common warts, flat warts and epidermodysplasia verruciformis, florid or oral papillomatoses and the proliferations which can be induced by ultraviolet radiation, in particular in the case of basal cell and prickle cell or spinocellularepithelioma;

(5) for treating other dermatological disorders, such as bullous dermatoses and collagen diseases;

(6) for treating certain opthalmological disorders, in particular corneopathies;

(7) for repairing or controlling/combating aging of the skin, whether photoinduced or chronologic, or for reducing actinic keratoses and pigmentations, or any pathology associated with chronologic or actinic aging;

(8) for preventing or treating the stigmata of epidermal and/or dermal atrophy induced by local or systemic corticosteroids, or any other form of cutaneous or skin atrophy;

(9) for preventing or treating disorders of cicatrization or for preventing or repairing stretch marks;

(10) for controlling disorders of the sebaceous function, such as acnehyperseborrhoea or simple seborrhoea;

(11) for the treatment or prevention of cancerous or precancerous states;

(12) for the treatment of inflammatory conditions such as arthritis;

(13) for the treatment of any condition of viral origin at the cutaneous or general level;

(14) for the prevention or treatment of alopecia;

(15) for the treatment of dermatological or general conditions manifesting an immunological component;

(16) for the treatment of ailments or conditions of the cardiovascular system, such as arteriosclerosis;

(17) for the treatment of respiratory conditions.

For the aforesaid therapeutic or pharmaceutical applications, the compounds according to the invention can advantageously be employed in combination with other retinoids, with ligands of RXR receptors, with vitamin D derivatives, with corticosteroids or estrogens, in combination with antioxidants, with anti-free radical agents, with $\alpha$-hydroxy or $\alpha$-keto acids or derivatives thereof, or with potassium-channel blockers.

Exemplary of the ligands of RXR receptors is cis-9-retinoic acid.

Exemplary D vitamins or derivatives thereof are the derivatives of vitamin $D_2$ or $D_3$ and, in particular, 1,25-dihydroxyvitamin $D_3$.

Exemplary compounds which control free radicals are $\alpha$-tocopherol, superoxide dismutase, ubiquinol or certain metal-chelating agents.

Exemplary $\alpha$-hydroxy or $\alpha$-keto acids or derivatives thereof are lactic, malic, citric, glycolic, mandelic, tartaric, glyceric or ascorbic acids, or salicylic acid derivatives or salts, amides or esters thereof.

Exemplary potassium-channel blockers include minoxidil (2,4-diamino-6-piperidinopyrimidine 3-oxide) and its derivatives.

The pharmaceutical/therapeutic compositions of the invention, intended especially for treating the aforesaid disease states, comprise a carrier, vehicle or diluent that is pharmaceutically acceptable, at least one compound of formula (I), or one of its optical or geometrical isomers, or salt or derivative thereof.

The administration of the compounds of formula (I) according to the invention can be carried out systemically, enterally, parenterally, topically or ocularly.

For enteral administration, the medicinal/pharmaceutical compositions may be in the form of tablets, hard gelatin capsules, dragees, syrups, suspensions, solutions, powders, granules, emulsions or polymeric or lipid microspheres or nanospheres or vesicles which permit controlled or precision release. For parenteral administration, the compositions may be in the form of solutions or suspensions for infusion or for injection.

The compounds of formula (I) according to the invention are generally administered at a daily dose of approximately 0.01 mg/kg to 100 mg/kg of body weight, and this at the regime or rate of 1 to 3 doses per diem.

For topical administration, the pharmaceutical compositions based on compounds according to the invention are more particularly intended for treating the skin and the mucosal membranes and are provided in the form of ointments, creams, milks, salves, powders, impregnated pads, solutions, gels, sprays, lotions or suspensions. They can also be provided in the form of polymeric or lipid vesicles or nanospheres or microspheres or of polymeric patches and of hydrogels permitting controlled release. These compositions for topical administration can be provided either in anhydrous form or in aqueous form, according to the particular clinical indication.

For ocular administration, they are principally eye washes.

These compositions for topical or ocular administration contain at least one compound of formula (I), or one of its optical or geometrical isomers or one of its salts or other derivatives thereof, at a concentration preferably ranging from 0.001% to 5% by weight relative to the total weight of the composition.

The compounds of formula (I) also find application in the cosmetics field, in particular in body and hair care and especially for the treatment of skin having a tendency to develop acne, for hair regrowth and combating hair loss, for combating the greasy appearance of the skin or the hair, in protecting the skin and hair against the deleterious effects of sunlight, or in the treatment of physiologically dry skin, and for preventing and/or for controlling photoinduced or chronologic aging.

For cosmetic applications, the compounds of formula (I) according to the invention may advantageously be employed in combination with other retinoids, with D vitamins or derivatives thereof, with corticosteroids, with compounds which control free radicals, with α-hydroxy or α-keto acids or derivatives thereof, or, alternatively, with ion-channel blockers, these various active agents employed with the compounds of the invention being as defined above.

The present invention, therefore, also features cosmetic compositions comprising, in a cosmetically acceptable vehicle, carrier or diluent, at least one compound of formula (I), or one of its optical or geometrical isomers or one of its salts or other derivative thereof. Such compositions are advantageously presented in the form of a cream, a milk, a lotion, a gel, polymeric or lipid vesicles or nanospheres or microspheres, a soap or a shampoo.

The concentration of the compound of formula (I) in the cosmetic compositions advantageously ranges from 0.001% to 3% by weight.

The medicinal and cosmetic compositions according to the invention may, in addition, contain inert or even pharmacodynamically or cosmetically active additives or combinations of these additives, and, especially: wetting agents; depigmenting agents such as hydroquinone, azelaic acid, caffeic acid or kojic acid; emollients; hydrating or moisturizing agents such as glycerol, PEG 400, thiamorpholinone and its derivatives, or urea; anti-seborrhoeic or anti-acne agents such as S-carboxymethylcysteine, S-benzylcysteamine, their salts and other derivatives thereof, or benzoyl peroxide; antibiotics such as erythromycin and esters thereof, neomycin, clindamycin and esters thereof, or tetracyclines; antifungal agents such as ketoconazole or 4,5-polymethylene-3-isothiazolinones; agents promoting hair regrowth, such as minoxidil (2,4-diamino-6-piperidinopyrimidine 3-oxide) and derivatives thereof, diazoxide (7-chloro-3-methyl-1,2,4-benzothiadiazine 1,1-dioxide) and phenytoin (5,4-diphenylimidazolidine-2,4-dione); non-steroidal anti-inflammatory agents; carotenoids and especially β-carotene; anti-psoriatic agents such as anthralin and derivatives thereof; and, lastly, eicosa-5,8,11, 14-tetraynoic and eicosa-5,8,11-triynoic acids and the esters and amides thereof.

The compositions according to the invention may also contain taste and flavor enhancers, such as the esters of para-hydroxybenzoic acid, stabilizing agents, moisture-regulating agents, pH-regulating agents, osmotic pressure-modifying agents, emulsifying agents, UV-A and UV-B screening agents and antioxidants such as α-tocopherol, butylated hydroxyanisole or butylated hydroxytoluene.

In order to further illustrate the present invention and the advantages thereof, the following specific examples are given, it being understood that same are intended only as illustrative and in nowise limitative.

(A) SYNTHESIS OF COMPOUNDS:

All of the compounds whose syntheses are set forth hereinbelow were characterized by proton NMR (250 MHz), mass spectrometry and elemental analysis.

EXAMPLE 1

Preparation of 1,2,3,4-tetrahydro-1,4a,9b-trimethyl-1,4-methanodibenzofuran:

50 g (0.267 mol) of bromoanisole, in solution in 120 ml of ethyl ether, were treated at 0° C. with 200 ml of n-butyllithium (1.6M in hexane) and the mixture was maintained under stirring at room temperature overnight. 41.57 g (273 mmol) of (+)-fenchone (Fluka) in 100 ml of ethyl ether were then added dropwise and the mixture was maintained under stirring for 6 h at room temperature. The reaction mixture was poured into 200 ml of a saturated ammonium chloride solution.

After extracting with 600 ml of ethyl ether, rinsing with water, drying over magnesium sulfate, filtering and evaporating, the residue was chromatographed on silica to yield 61.26 g (88%) of the expected intermediate, melting at 62°–64° C.

Method A:

57.5 g (0.276 mmol) of phosphorus pentachloride were added, at −10° C., to a suspension of 55.24 g (0.21 mol) of the above intermediate and of 4 g of calcium carbonate in 800 ml of chloroform.

The reaction mixture was stirred at room temperature for two hours, potassium carbonate (30 g) was then added and filtration was carried out. The solid residue was rinsed with chloroform and then chromatographed on silica in a hexane/$CH_2Cl_2$ (9/1) mixture to yield 31.5 g (65%) of the expected compound, melting at 68° C.

The same synthesis carried out from (−)-fenchone results in the dextrorotatory isomer of 1,2,3,4-tetrahydro-1,4a,9b-trimethyl-1,4-methanodibenzofuran, melting at 68° C.

Method B:

28.6 g of zinc chloride were added, at 0° C., to a solution of 55.24 g (0.21 mol) of the above intermediate in 800 ml of dichloromethane.

The reaction mixture was stirred at room temperature overnight, was then poured into 500 ml of ice-cold water and this mixture was then extracted with 500 ml of ether. After rinsing with water, drying over magnesium sulfate and evaporating, the product was isolated after chromatography. The solid residue was rinsed with chloroform and then chromatographed on silica in a hexane/$CH_2Cl_2$ (9/1) mixture to yield 19.8 g (41%) of the expected compound.

EXAMPLE 2

Preparation of 8-bromo-1,2,3,4-tetrahydro 1,4a,9b-trimethyl-1,4-methanodibenzofuran:

11.42 g (50 mmol) of (−)-1,2,3,4-tetra-hydro-1,4a,9b-trimethyl-1,4-methanodibenzofuran obtained in Example 1 were dissolved in 110 ml of tetrahydrofuran and were treated dropwise with a solution containing 8.9 g of N-bromosuccinimide (NBS) in 50 ml of dimethylformamide (DMF). The reaction mixture was maintained under stirring at room temperature for 2 h, 30 min, and was then poured into ice-cold water and extracted with 500 ml of ethyl ether. After rinsing with water, drying over magnesium sulfate, filtering and evaporating, 13.8 g (90%) of the expected derivative, melting at 119.8° C., were isolated after chromatography on silica in hexane.

EXAMPLE 3

Preparation of methyl 6-[(1,2,3,4-tetrahydro-1,4a,9b-trimethyl-1,4-methanodibenzofuran-8-yl)carbonyl]-2-naphthoate:

A solution of 5.96 g (26.1 mmol) of the compound obtained in Example 1 and 6.49 g (26.1 mmol) of 6-methoxycarbonyl-2-naphthoic acid chloride in 100 ml of dichloromethane was added dropwise to a suspension of 5.22 g (39.1 mmol) of aluminum chloride in 100 ml of anhydrous dichloromethane. The mixture was stirred for 4 hours at room temperature and was then poured into ice-cold water. After separation by settling, the aqueous phase was extracted with 500 ml of $CH_2Cl_2$. The organic phases were rinsed with water, dried over magnesium sulfate and evaporated.

After chromatography on silica in a $CH_2Cl_2$/hexane (9/1) mixture, 7.53 g (65%) of the expected compound, melting at 146° C., were isolated.

EXAMPLE 4

Preparation of 6-[1,2,3,4-tetrahydro-1,4a,9b-trimethyl-1,4-methanodibenzofuran-8-yl)carbonyl]-1-naphthoic acid:

7.52 g (17 mmol) of the methyl ester obtained in Example 3, in solution in 100 ml of methanol, were treated with 8 g of sodium hydroxide and heated at reflux for 3 h, 30 min. After evaporating, the residue was taken up in water and acidified to pH 1 with concentrated hydrochloric acid. The precipitate was filtered, rinsed with water and then recrystallized from methanol to yield 5.16 g (82%) of the expected compound, melting at 269.7° C.

EXAMPLE 5

Preparation of 6-[1,2,3,4-tetrahydro-1,4a,9b-trimethyl-1,4-methanodibenzofuran-8-yl)methyl]-2-naphthoic acid:

0.5 g (1.17 mmol) of the acid obtained in Example 4 was placed in 50 ml of palladium-on-charcoal (10%) under a pressure of 7 bar of hydrogen for 24 hours. The reaction mixture was filtered over Celite and then evaporated. The residue was chromatographed on silica in a $CH_2Cl_2$/ethyl ether (9/1) mixture to yield 110 mg (23%) of the expected compound, melting at 214°–216° C.

EXAMPLE 6

Preparation of methyl 6-[(1,2,3,4-tetrahydro-1,4a,9b-trimethyl-1,4-methanodibenzofuran-8-yl)hydroxymethyl]-2-naphthoate:

944 mg (2.14 mmol) of the ester obtained in Example 3, dissolved in 30 ml of a methanol/tetrahydrofuran (1/1) mixture, were treated with 81 mg of sodium borohydride. The reaction mixture was stirred for 5 hours at room temperature. Evaporation was carried out to dryness, the residue was taken up in ether and this phase was washed to neutral pH. After drying and evaporating, 905 mg (96%) of the expected compound, melting at 140°–141° C., were isolated.

EXAMPLE 7

Preparation of 6-[(1,2,3,4-tetrahydro-1,4a,9b-trimethyl-1,4-methanodibenzofuran-8-yl)hydroxymethyl]-2-naphthoic acid:

898 mg (2.03 mmol) of the ester obtained in Example 6, in 25 ml of methanol, were treated with 2 g of sodium hydroxide. The reaction mixture was maintained under stirring for 48 hours. The reaction mixture was poured into ice-cold water, acidified to pH 1 with concentrated hydrochloric acid and extracted with ethyl acetate. The organic phase was washed with water, dried over magnesium sulfate, filtered and evaporated to yield 951 mg (92%) of the expected compound, melting at 146°–148° C.

EXAMPLE 8

Preparation of methyl 4-[(1,2,3,4-tetrahydro-1,4a,9b-trimethyl-1,4-methanodibenzofuran-8-yl)carbonyl]benzoate:

5.92 g (44 mmol) of aluminum chloride were added portionwise to a solution of 6.76 g (29.6 mmol) of (+)-THTMDBF and 5.72 g (28.8 mmol) of the acid chloride of monomethyl terephthalate in 130 ml of $CH_2Cl_2$ and the reaction mixture was maintained under stirring at room temperature overnight.

After the same treatment as in Example 3, followed by chromatography on silica in a $CH_2Cl_2$/hexane (60/40) eluent mixture, 4.47 g (40%) of the expected compound, melting at 150° C., were isolated.

EXAMPLE 9

Preparation of 4-[(1,2,3,4-tetrahydro-1,4a,9b-trimethyl-1,4-methanodibenzofuran-8-yl)carbonyl]benzoic acid:

2.52 g (6.44 mmol) of the ester obtained in Example 8, in solution in 30 ml of methanol, were treated with 2.5 g of sodium hydroxide and heated at reflux for 3 hours. After the same treatment as in Example 7, followed by recrystallization from hexane, 2.35 g (97%) of the expected coompound, melting at 262°–264° C., are isolated.

EXAMPLE 10

Preparation of 4-[(1,2,3,4-tetrahydro-1,4a,9b-trimethyl-1,4-methanodibenzofuran-8-yl)hydroxymethyl]phenylcarbinol:

A solution of 3.76 g (10 mmol) of the acid obtained in Example 9 was added dropwise to a suspension of 1.14 g of lithium aluminium hydride in 10 ml of tetrahydrofuran and the reaction mixture was maintained under stirring for 3 hours at room temperature. The reaction mixture was neutralized at 0° C. by dropwise addition of a saturated ammonium chloride solution. The precipitate was filtered off, washed with hexane and dried to yield 3.13 g (86%) of the expected compound, melting at 113°–115° C.

EXAMPLE 11

Preparation of 4-[(1,2,3,4-tetrahydro-1,4a,9b-trimethyl-1,4-methanodibenzofuran-8-yl)carbonyl]benzaldehyde:

3.1 g (8.5 mmol) of the diol obtained in Example 10, in solution in 60 ml of $CH_2Cl_2$, were treated with 5.5 g of pyridinium chlorochromate. The reaction mixture was maintained under stirring at room temperature for 3 hours. The reaction mixture was then filtered through Celite. The organic phase was washed with a saturated ammonium chloride solution, rinsed with water, dried and evaporated to yield, after chromatography on silica in a $CH_2Cl_2$/hexane (9/1) eluent mixture, 2 g (66%) of the expected compound, melting at 138°–142° C.

EXAMPLE 12

Preparation of 2-(1,2,3,4-tetrahydro-1,4a,9b-trimethyl-1,4-methanodibenzofuran-8-yl)-2-(4-methoxycarbonylphenyl)-1,3-dioxolane:

2 g (5.12 mmol) of the ketone obtained in Example 8, in 20 ml of benzene, were treated with 0.5 ml of ethylene glycol and 10 mg of TsOH. The reaction mixture was heated at reflux for 24 hours and was then neutralized with a saturated sodium bicarbonate solution. After extraction with ethyl ether, the organic phase was washed with water, dried over magnesium sulfate, filtered and evaporated to yield, after chromatography on silica in a hexane/EtOAc (90/10)

mixture and triturating in hexane, 910 mg (41%) of the expected compound, melting at 136°–137° C.

EXAMPLE 13

Preparation of 2-(1,2,3,4-tetrahydro-1,4a,9b-trimethyl-1,4-methanodibenzofuran-8-yl)-2-(4-carboxyphenyl)-1,3-dioxolane:

0.87 g (2 mmol) of the methyl ester obtained in Example 12 was saponified under the conditions described in Example 4. After the same treatment and recrystallization from diisopropyl ether, 0.62 g (74%) of the expected compound, melting at 234°–236° C., was collected.

EXAMPLE 14

Preparation of 1,2,3,4-tetrahydro-1,4a,7,9b-tetramethyl-1,4-methanodibenzofuran:

12.7 g (63 mmol) of 2-methoxy-4-bromobenzene, in solution in 30 ml of ethyl ether, were treated at 0° C. with 47.5 ml of butyllithium (1.6M in hexane) and the mixture was maintained under stirring at room temperature overnight. 47.5 g (76 mmol) of (+)-fenchone (Fluka), in 100 ml of ethyl ether, were then added dropwise and the mixture was maintained under stirring for 6 h at room temperature. The reaction mixture was poured into 200 ml of a saturated ammonium chloride solution.

After extracting with 400 ml of ethyl ether, rinsing with water, drying over magnesium sulfate, filtering and evaporating, the residue was chromatographed on silica to yield 8.96 g (82%) of the expected intermediate compound, melting at 102°–103° C.

5.41 g (26 mmol) of phosphorus pentachloride were added, at −10° C., to a suspension of 5.48 g (21 mmol) of this intermediate and of 2.8 g of calcium carbonate in 50 ml of chloroform.

The reaction mixture was stirred at room temperature for two hours, potassium carbonate was then added and the reaction mixture was filtered. The solid residue was rinsed with chloroform and then chromatographed on silica in a hexane/$CH_2Cl_2$ (9/1) mixture to yield 2.75 g (57%) of the expected compound, in the form of a colorless oil.

EXAMPLE 15

Preparation of methyl 4-[(1,2,3,4-tetrahydro-1,4a,7,9b-tetramethyl-1,4-methanodibenzofuran-8-yl)carbonyl]benzoate:

1.43 g (10.7 mmol) of aluminum chloride was added portionwise to a solution of 1.7 g (7.1 mmol) of the compound obtained in Example 14 and 1.42 g (7.16 mmol) of the acid chloride of monomethyl terephthalate in 30 ml of $CH_2Cl_2$ and the reaction mixture was maintained under stirring at room temperature overnight.

After the same treatment as in Example 3, followed by chromatography on silica in a $CH_2Cl_2$/heptane (70/30) eluent mixture, 0.8 g (29%) of the expected compound, melting at 140°–142° C., was isolated; $[\alpha]_D=-6°$ (C=1, $CHCl_3$).

EXAMPLE 16

Preparation of 4-[(1,2,3,4-tetrahydro-1,4a,7,9b-tetramethyl-1,4-methanodibenzofuran-8-yl)carbonyl]benzoic acid:

0.83 g (2 mmol) of the ester obtained in Example 15, in solution in 10 ml of methanol, was treated with 0.8 g of sodium hydroxide and the mixture was maintained under stirring for 30 hours at room temperature. After the same treatment as in Example 7, followed by recrystallization from diisopropyl ether, 0.51 g (86%) of the expected compound, melting at 238°–239° C., was isolated; $[\alpha]_D=-28.3°$ (C=1, DMF)

EXAMPLE 17

Biological activity of the compound of Example 4:

| COMPOUND | Affinities for receptors Kd (nM) [a] | | | Antagonist activity with respect to the differentiation of F9 cells ($IC_{50}$, nM) [b] |
|---|---|---|---|---|
| | RAR α | RAR β | RAR ν | |
| Example 4 | 380 | 19 | 17 | 40 |

(a) The affinities for the RARs were determined under the conditions described in B. Martin et al, "Selective Synthetic Ligands for Human Nuclear Retinoic Acid Receptors," Skin Pharmacol., 5, 57–65 (1992).

(b) The antagonist activity was determined by coincubating a reference agonist (N-(4-carboxybenzyl)-5,6,7,8-tetrahydro-5,5,8,8-tetramethyl-2-naphthylamine (F9 $ICl_{50}=4$ nM)) and different concentrations of the retinoid to be tested. These experiments were carried out under conditions for the determination of activity with regard to F9 cell differentiation according to the technique described in M. Darmon, M. Rocher, M. T. Cavey, B. Martin, T. Rabilloud, C. Delescluse and B. Shroot, "Biological activity of retinoids correlates with affinity for nuclear receptors, but not for cytosolic binding protein," Skin Pharmacol., 1, 161–175 (1988).

(B) EXAMPLES OF FORMULATIONS:

(1) ORAL ROUTE:

EXAMPLE 18

The following composition was formulated in the form of a 0.8 g tablet:

| | |
|---|---|
| Compound of Example 4 | 0.005 g |
| Pregelatinized starch | 0.265 g |
| Microcrystalline cellose | 0.300 g |
| Lactose | 0.200 g |
| Magnesium stearate | 0.030 g |

For the treatment of acne, 1 to 3 tablets per day were administered to an adult individual for 3 to 6 months, depending on the seriousness of the case under treatment.

EXAMPLE 19

A suspension to be administered orally, to be packaged in 5 ml phials, was prepared:

| | |
|---|---|
| Compound of Example 4 | 0.050 g |
| Glycerol | 0.500 g |
| 70% Sorbitol | 0.500 g |
| Sodium saccharinate | 0.010 g |
| Methyl para-hydroxybenzoate | 0.040 g |
| Flavor q.s. | |
| Purified water q.s. for | 5 ml |

For the treatment of acne, one phial per day was administered to an adult individual for 3 months, depending on the seriousness of the case under treatment.

EXAMPLE 20

The following formulation, to be packaged in gelatin capsules, was prepared:

| | |
|---|---|
| Compound of Example 4 | 0.025 g |
| Maize starch | 0.060 g |
| Lactose q.s. for | 0.300 g |

The gelatin capsules were comprised of gelatin, titanium dioxide and a preservative.

For the treatment of psoriasis, 1 gelatin capsule per day was administered to an adult individual for 30 days.

(2) TOPICAL ROUTE:

EXAMPLE 21

The following nonionic water-in-oil cream was formulated:

| | |
|---|---|
| Compound of Example 4 | 0.100 g |
| Mixture of emulsifying lanolin alcohols and of refined waxes and oils, marketed by BDF under the trademark "Anhydrous eucerin" | 39.900 g |
| Methyl para-hydroxybenzoate | 0.075 g |
| Propyl para-hydroxybenzoate | 0.075 g |
| Sterile demineralized water q.s. for | 100.000 g |

This cream was applied to a psoriatic skin 1 to 2 times per day for 30 days.

EXAMPLE 22

A gel was formulated from the following composition:

| | |
|---|---|
| Compound of Example 4 | 0.050 g |
| Erythromycin base | 4.000 g |
| Butylated hydroxytoluene | 0.050 g |
| Hydroxypropylcellulose, marketed by Hercules under the trademark "Klucel HF" | 2.000 g |
| Ethanol (at 95°) q.s. for | 100.000 g |

This gel was applied to a skin affected by dermatosis or by acne 1 to 3 times per day for 6 to 12 weeks, depending on the seriousness of the case under treatment.

EXAMPLE 23

An antiseborrhoeic lotion was formulated by mixing the following ingredients:

| | |
|---|---|
| Compound of Example 4 | 0.030 g |
| Propylene glycol | 5.000 g |
| Butylated hydroxytoluene | 0.100 g |
| Ethanol (at 95°) q.s for | 100.000 g |

This lotion was applied twice per day to a seborrhoeic scalp and a significant improvement was observed within a period of between 2 and 6 weeks.

EXAMPLE 24

A cosmetic composition to counter the harmful effects of the sun was formulated by mixing the following ingredients:

| | |
|---|---|
| Compound of Example 5 | 1.000 g |
| Benzylidenecamphor | 4.000 g |
| Fatty acid triglycerides | 31.000 g |

-continued

| | |
|---|---|
| Glyceryl monostearate | 6.000 g |
| Stearic acid | 2.000 g |
| Cetyl alcohol | 1.200 g |
| Lanolin | 4.000 g |
| Preservatives | 0.300 g |
| Propylene glycol | 2.000 g |
| Triethanolamine | 0.500 g |
| Fragrance | 0.400 g |
| Demineralized water q.s for | 100.000 g |

This composition was applied daily. It was effective against photoinduced aging.

EXAMPLE 25

The following nonionic oil-in-water cream was formulated:

| | |
|---|---|
| Compound of Example 5 | 0.500 g |
| Vitamin D$_3$ | 0.020 g |
| Cetyl alcohol | 4.000 g |
| Glyceryl monostearate | 2.500 g |
| PEG 50 stearate | 2.500 g |
| Karite butter | 9.200 g |
| Propylene glycol | 2.000 g |
| Methyl para-hyroxybenzoate | 0.075 g |
| Propyl para-hydroxybenzoate | 0.075 g |
| Sterile demineralized water q.s. for | 100.000 g |

This cream was applied to a psoriatic skin to 2 times per day for 30 days.

EXAMPLE 26

A topical gel was formulated by mixing the following ingredients:

| | |
|---|---|
| Compound of Example 13 | 0.050 g |
| Ethanol | 43.000 g |
| α-Tocopherol | 0.050 g |
| Carboxyvinyl polymer, marketed under the trademark "Carbopol 941" by Goodrich | 0.500 g |
| Triethanolamine, as a 20% by weight aqueous solution | 3.800 g |
| Water | 9.300 g |
| Propylene glycol q.s. for | 100.000 g |

This gel was applied in the treatment of acne to 3 times per day for 6 to 12 weeks, depending on the seriousness of the case under treatment.

EXAMPLE 27

A hair lotion for combating hair loss and for promoting hair regrowth was formulated by mixing the following ingredients:

| | |
|---|---|
| Compound of Example 13 | 0.05 g |
| Compound marketed under the trademark "Minoxidil" | 1.00 g |
| Propylene glycol | 20.00 g |
| Ethanol | 34.92 g |
| Polyethylene glycol (molecular weight = 400) | 40.00 g |
| Butylated hydroxyanisole | 0.01 g |
| Butylated hydroxytoluene | 0.02 g |
| Water q.s. for | 100.00 g |

This lotion was applied twice per day for 3 months to a scalp which had suffered significant hair loss.

EXAMPLE 28

An anti-acne cream was formulated by mixing the following ingredients:

| | |
|---|---|
| Compound of Example 6 | 0.050 g |
| Retinoic acid | 0.010 g |
| Mixture of glyceryl and polyethylene glycol stearates (75 mol), marketed under the trademark of "Gelot 64" by Gattefosse | 15.000 g |
| Kernel Oil polyoxyethylenated with 6 mol of ethylene oxide, marketed under the trademark "Labrafil M2 130 CS" by Gattefosse | 8.000 g |
| Perhydrosqualene | 10.000 g |
| Preservatives | q. s. |
| Polyethylene glycol (molecular weight = 400) | 8.000 g |
| Disodium salt of ethylenediaminetetra-acetic acid | 0.050 g |
| Purified water q.s. for | 100.00 g |

This cream was applied to a skin affected by dermatosis or by acne 1 to 3 times per day for 6 to 12 weeks.

EXAMPLE 29

An oil-in-water cream was formulated from the following composition:

| | |
|---|---|
| Compound of Example 7 | 0.020 g |
| Betamethasone 17-valerate | 0.050 g |
| S-Carboxymethylcysteine | 3.000 g |
| Polyoxyethylene stearate (40 mol of ethylene oxide), marketed under the trademark "Myrj 52" by Atlas | 4.000 g |
| Sorbitan monolaurate, polyoxyethylenated with 20 mol of ethylene oxide, marketed under the trademardk "Tween 20" by Atlas | 1.800 g |
| Mixture of glyceryl mono- and distearate, marketed under the trade,arl "Geleol" by Gattefosse | 4.200 g |
| Propylene glycol | 10.000 g |
| Butylated hydroxyanisole | 0.010 g |
| Butylated hydroxytoluene | 0.020 g |
| Cetostearyl alcohol | 6.200 g |
| Preservatives | q.s. |
| Perhydrosqualene | 18.000 g |
| Mixture of caprylic/capric triglycerides marketed under the trademark "Miglyol 812" by Dynamit Nobel | 4.000 g |
| Triethanaolamine (99% by weight) | 2.500 g |
| Water q.s. for | 100.00 g |

This cream was applied 2 times per day for 30 days to a skin affected by dermatosis.

EXAMPLE 30

The following cream of oil-in-water type was formulated:

| | |
|---|---|
| Lactic acid | 5.000 g |
| Compound of Example 12 | 0.020 g |
| Polyoxyethylene stearate (40 mol of ethylene oxide), marketed under the trademark "Myrj 52" by Atlas | 4.000 g |
| Sorbitan monolaurate, polyoxyethylenated with 20 mol of ethylene oxide, marketed under the trademark "Tween 20" by Atlas | 1.800 g |
| Mixture of glyceryl mono- and distearate, marketed under the trademark "Geleol" by Gattefosse | 4.200 g |
| Propylene glycol | 10.000 g |
| Butylated hydroxyanisole | 0.010 g |
| Butylated hydroxytoluene | 0.020 g |
| Cetostearyl alcohol | 6.200 g |
| Preservatives | q.s. |
| Perhydrosqualene | 18.000 g |
| Mixture of caprylic/capric triglycerides, marketed under the trademark "Miglyol 812" by Dynamit Nobel | 4.000 g |
| Water q.s. for | 100.000 g |

This cream was applied once per day. It assisted in combating aging, whether photoinduced or chronologic.

While the invention has been described in terms of various preferred embodiments, the skilled artisan will appreciate that various modifications, substitutions, omissions, and changes may be made without departing from the spirit thereof. Accordingly, it is intended that the scope of the present invention be limited solely by the scope of the following claims, including equivalents thereof.

What is claimed is:

1. A dibenzofuran compound having the structural formula (I):

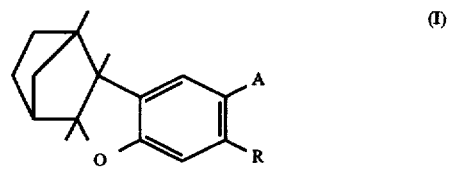

in which R is a hydrogen atom, a halogen atom, a lower alkyl radical having 1 to 6 carbon atoms, a lower acyl radical having 1 to 10 carbon atoms or an OR' radical; A is a radical selected from the group consisting of the following formulae (IIa–IIc):

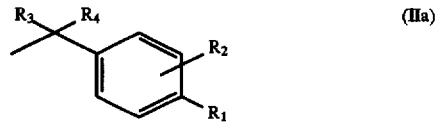

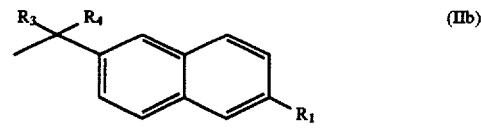

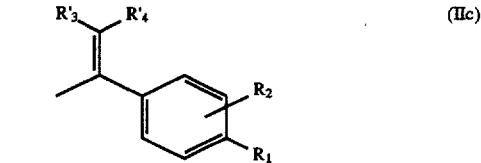

wherein $R_1$ is (i) a hydrogen atom, (ii) the —$CH_3$ radical, (iii) an —$CH_2$—O—$R_5$ radical, (iv) an —$OR_5$ radical (v) a

radical, or (vi) an —S(O),R$_6$ radical; R$_2$ is a hydrogen atom or an —OR$_5$ radical; R$_3$ and R$_4$ are independently a hydrogen atom, a lower alkyl radical having 1 to 6 carbon atoms or a —(X)$_n$—(CH$_2$)$_m$—R$_7$ radical, or R$_3$ and R$_4$ may together form an oxo (═O) group, a thioxo (═S) group, an oxime group or a group derived from the oxime (R$_6$—O—N═), an epoxy group, or a dioxolane group (—O—(CH$_2$)$_q$—O—) wherein q is equal to 2 or 3; R$_3$' and R$_4$' are independently a hydrogen atom, a lower alkyl radical having 1 to 6 carbon atoms or a lower acyl radical having 1 to 6 carbon atoms; t is equal to 0, 1 or 2; R$_5$ is a hydrogen atom, a lower alkyl radical having 1 to 6 carbon atoms, or a lower acyl radical having 1 to 6 carbon atoms; R$_6$ is a hydrogen atom, an —N(R',R''') radical, or an —OR$_8$ radical; R$_6$ is a hydrogen atom or a —(CO)$_p$—R$_9$ radical, wherein p is 0 or 1; R$_8$ and R' are independently a hydrogen atom, an alkyl radical having from 1 to 20 carbon atoms, a mono- or polyhydroxyalkyl radical respectively having 1 to 6 or 2 to 6 carbon atoms, an optionally substituted phenyl radical or optionally substituted benzyl or phenethyl radical wherein the substituents on said phenyl, benzyl or phenethyl radical, if present, are selected from the group consisting of halogen, hydroxyl, nitro and methoxy groups; R$_9$ is a hydrogen atom, an alkyl radical, having 1 to 20 carbon atoms, an alkenyl radical which is a linear or branched radical having 1 to 20 carbon atoms and having at least one ethylenic double bond, an alkynyl radical, which is a linear or branched radical having 1 to 20 carbon atoms and having at least one acetylenic double bond, a phenyl radical, an —OR$_7$ radical wherein m is other than 0, or an —N(R',R''') radical; R' and R''', which may be identical or different, are each a hydrogen atom, a lower alkyl radical having 1 to 6 carbon atoms, a mono- or polyhydroxyalkyl radical respectively having 1 to 6 or 2 to 6 carbon atoms, an optionally substituted phenyl radical, an optionally substituted benzyl or phenethyl radical wherein the substituents on said phenyl, benzyl or phenethyl radical, if present, are selected from the group consisting of halogen, nitro, hydroxyl and methoxy group; X is an oxygen or sulfur atom; and n ranges from 0 to 1 and m from 0 to 10; or a pharmaceutically/cosmetically acceptable salt or optical or geometric isomer thereof.

2. A dibenzofuran compound as defined by claim 1, wherein formula (I), A has the structure (IIa).

3. A dibenzofuran compound as defined by claim 1, wherein formula (I), A has the structure (IIb).

4. A dibenzofuran compound as defined by claim 1, wherein formula (I), A has the structure (IIc).

5. A dibenzofuran compound as defined by claim 1, comprising a pharmaceutically acceptable salt thereof.

6. A dibenzofuran compound as defined by claim 1, wherein formula (I), the lower alkyl radical substituents are selected from the group consisting of methyl, ethyl, isopropyl, butyl, tert-butyl and hexyl radicals.

7. A dibenzofuran compound as defined by claim 1, wherein formula (I), the lower acyl radical is selected from the group consisting of acetyl, propionyl and pivaloyl radicals.

8. A dibenzofuran compound as defined by claim 1, wherein formula (I), the monohydroxyalkyl radical substituents are selected from the group consisting of 2-hydroxyethyl, 2-hydroxypropyl and 3-hydroxypropyl radicals.

9. A dibenzofuran compound as defined by claim 1, wherein formula (I), the polyhydroxyalkyl radical substituents are selected from the group consisting of 2,3-dihydroxypropyl, 2,3,4-trihydroxybutyl, 2,3,4,5-tetrahydroxypentyl and pentaerythritol radicals.

10. A dibenzofuran compound as defined by claim 1, selected from the group consisting of methyl 6-[(1,2,3,4-tetrahydro-1,4a,9b-trimethyl-1,4-methanodibenzofuran-8-yl)carbonyl]-2-naphthoate; 6-[(1,2,3,4-tetrahydro-1,4a,9b-trimethyl-1,4-methanodibenzofuran-8-yl)carbonyl]-2-naphthoic acid; 6-[(1,2,3,4-tetrahydro-1,4a,9b-trimethyl-1,4-methanodibenzofuran-8-yl)methyl]-2-naphthoic acid; methyl 6-[(1,2,3,4-tetrahydro-1,4a,9b-trimethyl-1,4-methanodibenzofuran-8-yl)hydroxymethyl]-2-naphthoate; 6-[(1,2,3,4-tetrahydro-1,4a,9b-trimethyl-1,4-methanodibenzofuran-8-yl)hydroxymethyl]-2-naphthoic acid; methyl 4-[(1,2,3,4-tetrahydro-1,4a,9b-trimethyl-1,4-methanodibenzofuran-8-yl)carbonyl]benzoate; 4-[(1,2,3,4-tetrahydro-1,4a,9b-trimethyl-1,4-methanodibenzofuran-8-yl)carbonyl]benzoic acid; 4-[(1,2,3,4-tetrahydro-1,4a,9b-trimethyl-1,4-methanodibenzofuran-8-yl)hydroxymethyl] phenylcarbinol; 4-[(1,2,3,4-tetrahydro-1,4a,9b-trimethyl-1,4-methanodibenzofuran-8-yl)carbonyl]benzaldehyde; 2-(1,2,3,4-tetrahydro-1,4a,9b-trimethyl-1,4-methanodibenzofuran-8-yl)-2-(4-methoxycarbonylphenyl)-1,3-dioxolane; 2-(1,2,3,4-tetrahydro-1,4a,9b-trimethyl-1,4-methanodibenzofuran-8-yl)-2-(4-carboxyphenyl)-1,3-dioxolane; 1,2,3,4-tetrahydro-1,4a,7,9b-tetramethyl-1,4-methanodibenzofuran; methyl 4-[(1,2,3,4-tetrahydro-1,4a,7,9b-tetramethyl-1,4-methanodibenzofuran-8-yl)carbonyl] benzoate; and 4-[(1,2,3,4-tetrahydro-1,4a,7,9b-tetramethyl-1,4-methanodibenzofuran-8-yl)carbonyl]benzoic acid.

11. A dibenzofuran compound as defined by claim 3, wherein formula (IIb), R$_1$ is the radical:

12. A dibenzofuran compound having the structural formula (X):

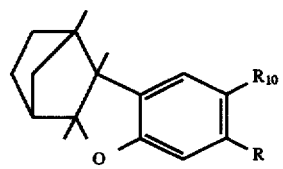

in which R is as defined in claim 1; and R$_{10}$ has the definition of R$_1$ in claim 1, with the proviso that R$_{10}$ can not be a hydrogen atom, and wherein R$_1$ further can be a moiety selected from the group consisting of a halogen atom, a —C(O)—R$_8$ radical, a —C(O)—CH$_2$-halogen radical, or a (CH$_2$)$_n$N(R',R''') radical, wherein R$_8$, R', R''' and n are also as defined in claim 1.

13. A dibenzofuran compound as defined by claim 11, selected from the group consisting of 1,2,3,4-tetrahydro-1,4a,9b-trimethyl-1,4-methanodibenzofuran-8-yl methyl ketone; 1,2,3,4-tetrahydro-1,4a,9b-trimethyl-1,4-methanodibenzofuran-8-carboxaldehyde; 1,2,3,4-tetrahydro-1,4a,9b-trimethyl-1,4-methanodibenzofuran-8-carboxylic acid; 1,2,3,4-tetrahydro-1,4a,9b-trimethyl-1,4-methanodibenzofuran-8-yl bromomethyl ketone; and 8-ethynyl-1,2,3,4-tetrahydro-1,4a,9b-trimethyl-1,4-methanodibenzofuran.

14. A pharmaceutical composition of matter, comprising a therapeutically effective amount of a dibenzofuran compound as defined by claim 1, or pharmaceutically acceptable salt or isomer thereof, and a pharmaceutically acceptable carrier or diluent therefor.

15. The pharmaceutical composition as defined by claim 14, further comprising a retinoid compound, a D vitamin a corticosteroid, an anti-free radical agent, an α-hydroxy or α-keto acid an ion channel blocker, or combination thereof.

16. The pharmaceutical composition as defined by claim 14, selected from the group consisting of a tablet, a capsule, a syrup, a suspension, an elixir, a solution, a powder, granules, an emulsion, microspheres, nanospheres, lipid vesicles, polymeric vesicles, or a composition for injection.

17. The pharmaceutical composition as defined by claim 14, selected from the group consisting of an ointment, a cream, a milk, a pommade, an impregnated pad, a gel, a spray, and a lotion.

18. The pharmaceutical composition as defined by claim 14, for topical administration.

19. The pharmaceutical composition as defined by claim 14, for systemic administration.

20. The pharmaceutical composition as defined by claim 14, comprising from 0.001% to 5% by weight of said dibenzofuran compound, or salt or isomer thereof.

21. A cosmetic composition of matter, comprising a cosmetically effective amount of a dibenzofuran compound as defined by claim 1, or cosmetically acceptable salt or isomer thereof, and a cosmetically acceptable carrier or diluent therefor.

22. The cosmetic composition as defined by claim 21, selected from the group consisting of a cream, a milk, a lotion, a gel, microspheres, nanospheres, lipid vesicles, polymeric vesicles, a soap, and a shampoo.

23. The cosmetic composition as defined by claim 21, comprising from 0.001% to 3% by weight of said dibenzofuran compound, or salt or isomer thereof.

24. The cosmetic composition as defined by claim 21, further comprising a compound selected from the group consisting of retinoid compound, a D vitamin a corticosteroid, an anti-free radical agent, an α-hydroxy or α-keto acid an ion channel blocker, and combinations thereof.

25. The pharmaceutical composition as defined by claim 14, further comprising a compound selected from the group consisting of a wetting agent, a depigmenting agent, a moisturizing agent, an antiseborrhoeic or antiacne agent, an antibiotic, an antifungal agent, a hair regrowth promoter, a non-steroidal anti-inflammatory agent, a carotenoid, an anti-psoriatic agent, 5,8,11,14-eicosatetraytnoic, 5,8,11-eicosatrynoic acid or a pharmaceutically acceptable ester or amide thereof, and combinations thereof.

26. The pharmaceutical composition as defined by claim 14, further comprising a compound selected from the group consisting of a taste- or flavor-enhancing agent, a preservative, a stabilizer, a moisture regulating agent, a pH regulating agent, an osmotic pressure modifying agent, an emulsifying agent, a UV-A or UV-B screening agent, an antioxidant, and combinations thereof.

27. The cosmetic composition by claim 21, further comprising a compound selected from the group consisting of a wetting agent, a depigmenting agent, a moisturizing agent, an antiseborrhoeic or antiacne agent, an antibiotic, an antifungal agent, a hair regrowth promoter, a non-steroidal anti-inflammatory agent, a carotenoid, an anti-psoriatic agent, 5,8,11-14-eicosatetraynoic, 5,8,11-eicosatrynoic acid or cosmetically acceptable ester or amide thereof, and combinations thereof.

28. The cosmetic composition as defined by claim 21, further comprising a compound selected from the group consisting of a taste- or flavor-enhancing agent, a preservative, a stabilizer, a moisture regulating agent, a pH regulating agent, an osmotic pressure modifying agent, an emulsifying agent, a UV-A or UV-B screening agent, an antioxidant, and combinations thereof.

* * * * *